(12) United States Patent
Inamura

(10) Patent No.: US 12,702,274 B2
(45) Date of Patent: Aug. 11, 2026

(54) SIGNAL CABLE, ENDOSCOPE, AND METHOD OF PROCESSING SIGNAL CABLE

(71) Applicant: OLYMPUS MEDICAL SYSTEMS CORP., Tokyo (JP)

(72) Inventor: Masaru Inamura, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 224 days.

(21) Appl. No.: 18/537,261

(22) Filed: Dec. 12, 2023

(65) Prior Publication Data

US 2024/0122454 A1 Apr. 18, 2024

Related U.S. Application Data

(63) Continuation of application No. PCT/JP2021/022731, filed on Jun. 15, 2021.

(51) Int. Cl.

*A61B 1/00* (2006.01)
*H04N 23/50* (2023.01)

(52) U.S. Cl.

CPC ....... *A61B 1/00114* (2013.01); *A61B 1/00124* (2013.01); *H04N 23/555* (2023.01)

(58) Field of Classification Search

CPC ............ A61B 1/00114; A61B 1/00124; H04N 23/555

See application file for complete search history.

(56) References Cited

U.S. PATENT DOCUMENTS

| | | | | |
|---|---|---|---|---|
| 2010/0236810 A1* | 9/2010 | Mukai | ...................... | H01Q 9/30 174/105 R |
| 2013/0064530 A1* | 3/2013 | Sekido | ............... | A61B 1/00124 396/17 |
| 2013/0341065 A1* | 12/2013 | Sato | .................. | H01B 11/1895 174/107 |

FOREIGN PATENT DOCUMENTS

| | | |
|---|---|---|
| JP | H08-271809 A | 10/1996 |
| JP | 2005-261522 A | 9/2005 |
| JP | 2007-134137 A | 5/2007 |
| JP | 2010-250973 A | 11/2010 |
| JP | 2011-238458 A | 11/2011 |
| WO | 2011/142322 A1 | 11/2011 |

OTHER PUBLICATIONS

International Search Report dated Sep. 7, 2021 received in PCT/JP2021/022731.

* cited by examiner

*Primary Examiner* — Aaron B Fairchild

(74) *Attorney, Agent, or Firm* — Scully, Scott, Murphy & Presser, P.C.

(57) ABSTRACT

A signal cable includes: a plurality of electric wires; a first insulating layer surrounding the plurality of electric wires; a shielding layer covering a circumference of the first insulating layer; a second insulating layer covering a circumference of the shielding layer; and a fixing portion fixing a distal end portion of the shielding layer, in which distal end portions of electric wires protrude more toward a distal end side than a distal end portion of the second insulating layer, the distal end portion of shielding layer is disposed nearer to the proximal end side than a distal end portion of the first insulating layer and the distal end portion of the second insulating layer, and the fixing portion fixes the distal end portion of the shielding layer in a space between the distal (Continued)

end portion of the first insulating layer and the distal end portion of the second insulating layer.

5 Claims, 9 Drawing Sheets

SIGNAL CABLE, ENDOSCOPE, AND METHOD OF PROCESSING SIGNAL CABLE

CROSS REFERENCE TO RELATED APPLICATION

This application is a continuation application of PCT/JP2021/022731 filed on Jun. 15, 2021, the entire contents of which are incorporated herein by this reference.

BACKGROUND OF THE INVENTION

1. Field of the Invention

The present invention relates to a signal cable, an endoscope, and a method of processing the signal cable, particularly to a signal cable to be connected to an electric circuit disposed at a distal end portion of an insertion section of an endoscope, an endoscope provided with the signal cable, and a method of processing the signal cable.

2. Description of the Related Art

Conventionally, an endoscope has been known in which an image pickup device and an electric circuit such as a drive circuit for driving the image pickup device are disposed in a distal end portion of an insertion section of the endoscope. An endoscope of this type includes an insertion section provided with a signal cable for connecting the electric circuit disposed in the distal end portion to a predetermined electric circuit disposed on the proximal end side.

The signal cable disposed in the insertion section of the endoscope includes a power line for supplying electric power to the image pickup device disposed in the distal end portion, and a plurality of signal lines and the like for transmitting predetermined signals for driving the image pickup device. In general, the plurality of signal lines and the like are bundled together and comprehensively provided with a shielding layer (hereinafter referred to as a comprehensive shield), which is further covered with an outer cover (hereinafter referred to as a comprehensive outer cover).

If such a comprehensive shield, which is often made of a metal material, is provided to unnecessarily cover the distal end portion, the distal end portion would become more rigid and affect bending performance of the cable. Japanese Patent Application Laid-Open Publication No. 1-18-271809 suggests an endoscope produced by temporarily stripping the comprehensive outer cover and the comprehensive shield and then shifting the comprehensive outer cover in such a manner that the comprehensive outer cover is drawn forward followed by fixation, in order to improve the bending performance of the signal cable without increasing the length of the rigid part in the distal end portion of the endoscope.

SUMMARY OF THE INVENTION

A signal cable according to one aspect of the present invention includes: a plurality of electric wires that are all disposed so as to extend in a longitudinal direction from a distal end toward a proximal end side and are configured to transmit electricity; a first insulating layer that surrounds the plurality of electric wires and is disposed so as to extend in the longitudinal direction; a shielding layer that covers a circumference of the first insulating layer and is disposed so as to extend in the longitudinal direction; a second insulating layer that covers a circumference of the shielding layer and is disposed so as to extend in the longitudinal direction; and a fixing portion that fixes a distal end portion of the shielding layer, in which distal end portions of the electric wires are disposed so as to protrude more toward a distal end side than a distal end portion of the second insulating layer, the distal end portion of the shielding layer is disposed nearer to the proximal end side than a distal end portion of the first insulating layer and the distal end portion of the second insulating layer, and the fixing portion fixes the distal end portion of the shielding layer in a space generated between the distal end portion of the first insulating layer and the distal end portion of the second insulating layer so as to maintain a state where at least the distal end portion of the shielding layer is not exposed from a distal end of the second insulating layer.

An endoscope according to one aspect of the present invention includes: an electric circuit board; a plurality of electric wires that are all disposed so as to extend in a longitudinal direction from a distal end toward a proximal end side and are configured to transmit electricity to the electric circuit board; a first insulating layer that surrounds the plurality of electric wires and is disposed so as to extend in the longitudinal direction; a shielding layer that covers a circumference of the first insulating layer and is disposed so as to extend in the longitudinal direction; a second insulating layer that covers a circumference of the shielding layer and is disposed so as to extend in the longitudinal direction; and a fixing portion that fixes a distal end portion of the shielding layer, in which distal end portions of the electric wires are disposed so as to protrude more toward a distal end side than a distal end portion of the second insulating layer, the distal end portion of the shielding layer is disposed nearer to the proximal end side than a distal end portion of the first insulating layer and the distal end portion of the second insulating layer, and the fixing portion fixes the distal end portion of the shielding layer in a space generated between the distal end portion of the first insulating layer and the distal end portion of the second insulating layer so as to maintain a state where at least the distal end portion of the shielding layer is not exposed from a distal end of the second insulating layer.

A method of processing a signal cable that includes: a plurality of electric wires that are disposed so as to extend in a longitudinal direction from a distal end toward a proximal end side and are configured to transmit electricity; a first insulating layer that surrounds the plurality of electric wires and is disposed so as to extend in the longitudinal direction; a shielding layer that covers a circumference of the first insulating layer and is disposed so as to extend in the longitudinal direction; and a second insulating layer that covers a circumference of the shielding layer and is disposed so as to extend in the longitudinal direction according to one aspect of the present invention includes: aligning one ends of the plurality of electric wires, one end of the first insulating layer, one end of the shielding layer, and one end of the second insulating layer; cutting the second insulating layer on a distal end side; culling the shielding layer on a distal end side; cutting the first insulating layer on a distal end side; applying an adhesive to the distal end side of the first insulating layer and to the distal end side of the shielding layer; drawing the second insulating layer having been cut toward the distal end side; and forming a fixing portion that fixes a distal end portion of the shielding layer in a space generated between a distal end portion of the first insulating layer and a distal end portion of the second insulating layer by causing the adhesive to cure so as to maintain a state where the distal end portion of the shielding layer is not exposed from a distal end of the second insulating layer.

BRIEF DESCRIPTION OF THE DRAWINGS

FIG. 3 is a cross-sectional view illustrating a cross section in the longitudinal direction and a cross section perpendicular to the longitudinal direction of the distal end portion of the signal cable according to the first embodiment;

DETAILED DESCRIPTION OF THE PREFERRED EMBODIMENTS

Connection of a signal cable disposed in an insertion section of an endoscope to an electric circuit board is generally accompanied by manual procedures including, for example, twisting the signal cable, whereas the procedure of drawing the comprehensive outer cover according to the technique described in above-mentioned Japanese Patent Application Laid-Open Publication No, H8-271809 readily involves variation in drawing direction, and therefore, it may be difficult to connect such a signal cable, and the signal cable may take an excessive strain because of twisting. Furthermore, the end of the comprehensive shield inside the comprehensive outer cover is not restricted and therefore can come into contact with other internal signal lines.

Japanese Patent Application Laid-Open Publication No. 2005-261522 suggests a technique of preventing reduction in work efficiency resulting from the variation described above by fitting a ring-shaped conductive member onto the outer cover of the signal cable and meanwhile temporarily drawing forward a shield line disposed inside the outer cover and then bending back the shield line along the ring-shaped member.

However, according to the technique suggested in Japanese Patent Application Laid-Open Publication No. 2005-261522 mentioned above, a ring-shaped conductive member is provided on the outer cover of the signal cable, which causes a problem of increase in the number of components and increase in outer diameter of the signal cable itself.

According to the present invention, a signal cable and an endoscope can be provided which are improved in work efficiency of processing the end portion of the comprehensive shield and are not potentially deteriorated in quality without dimensional increase in the radial direction.

Embodiments of the present invention will be described below with reference to the drawings.

First Embodiment

Figure 1:
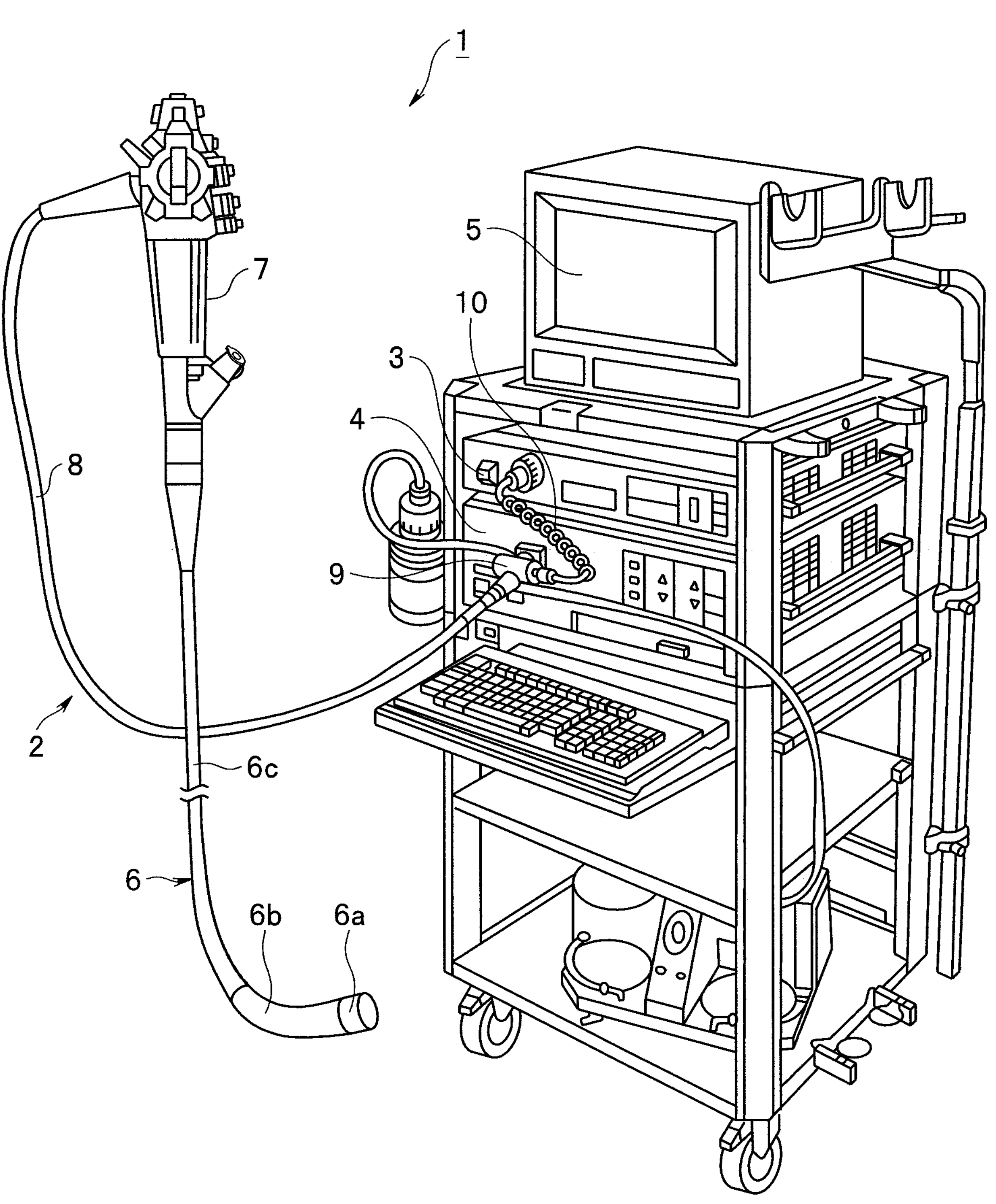
FIG. 1 is an external perspective view illustrating a configuration of an endoscope system including an endoscope that incorporates a signal cable according to a first embodiment of the present invention.

FIG. 1 is an external perspective view of a main part illustrating a configuration of an endoscope system including an endoscope that incorporates a signal cable according to a first embodiment of the present invention.

As shown in FIG. 1, an endoscope system 1 according to the first embodiment of the present invention includes an endoscope 2 used to observe a subject and pick up an image of the subject, a video processer 3 connected to the endoscope 2 to receive an image-pickup signal from the endoscope 2 and perform predetermined image processing, a light source device 4 for supplying illumination light for illuminating the subject, and a monitoring device 5 for displaying an observation image in response to the image-pickup signal.

<Configuration of Endoscope 2>

The endoscope 2 includes an elongated insertion section 6 to be inserted into a body cavity or the like of the subject, an operation section 7 that is disposed on the proximal end side of the insertion section 6 and is to be grasped by an operator performing an operation, and a universal cord 8 having one end portion extending from a side portion of the operation section 7.

The insertion section 6 is flexible and has an elongated shape in addition, the insertion section 6 includes a rigid distal end portion 6*a*, a bending portion 6*b* that is bendable, and a long flexible tube portion 6*c* having flexibility, in this order from the distal end side.

The distal end portion 6*a* of the insertion section 6 includes an objective optical system (not illustrated) including a lens through which light is transmitted to form an object image, an image pickup device disposed on an image-forming plane of the objective optical system, and an electric circuit board 12 (see FIG. 2) mounted with predetermined electronic components for driving the image pickup device. The electric circuit board 12 is connected to a distal end portion of an electric cable that incorporates a plurality of electric wires. An electric cable of this type will be described later taking a signal cable 11 (see FIG. 2 and the like) as an example, which includes a signal line and the like for transmitting predetermined electric signals for driving various electronic components such as the image pickup device. Examples of the electric cable include not only the signal cable 11 but also a feeder cable configured to supply electricity as energy for driving various electronic components such as the image pickup device, and a signal/feeder cable formed of a bundle of electric cables including a signal cable and a feeder cable.

Note that, according to the present embodiment as described above, the image pickup device is a solid-state image pickup device including a CMOS image sensor and a CCD image sensor, for example, and is configured to perform photoelectric conversion on an object and output predetermined image-pickup signals to the subsequent stage.

The interior of the insertion section 6, the operation section 7, and the universal cord 8 is provided with a light guide (not illustrated) for transmitting illumination light supplied from the light source device 4 and the above-described signal cable 11.

The universal cord 8 is provided with a connector 9 on the proximal end side, and the connector 9 is detachably connected to the light source device 4. An electric contact part is provided on a side face of the connector 9, and one end of a connecting cable 10 is connected to the electric contact part. The connecting cable 10 incorporates a signal line and the like for transmitting image-pickup signals from the image pickup device of the endoscope 2, for example, and a connector portion on the other end of the connecting cable 10 is connected to the video processer 3.

<Signal Cable 11>

Next, the signal cable 11 according to the present embodiment will be described with reference to FIGS. 2 and 3.

Figure 2:
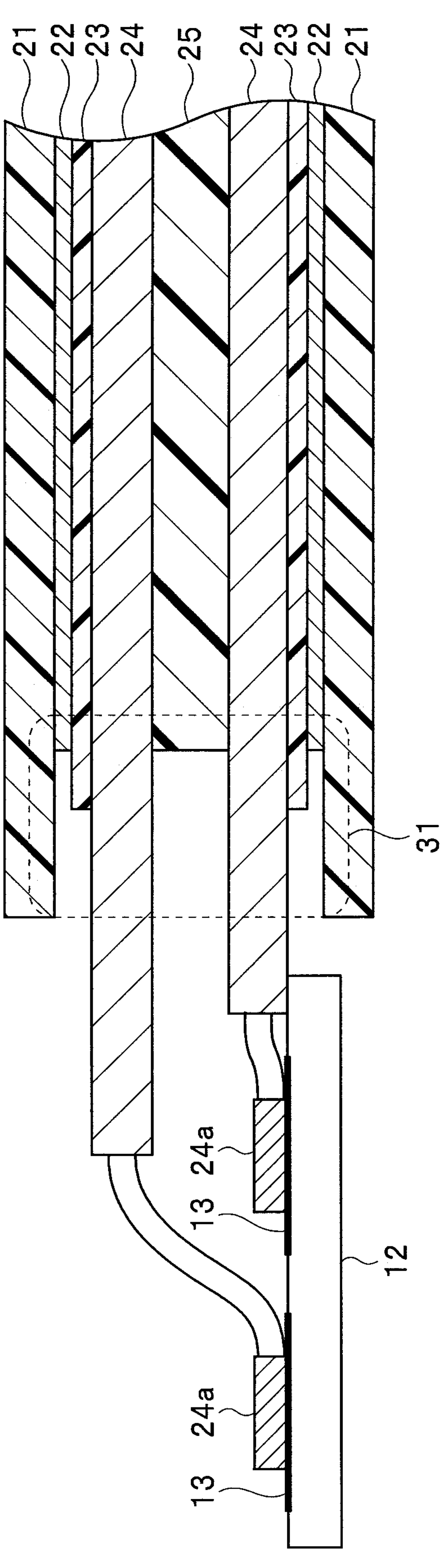
FIG. 2 is an enlarged cross-sectional view of a main part illustrating the state where signal lines in a distal end portion of the signal cable according to the first embodiment are connected to terminal portions of an electric circuit board.

FIG. 2 is an enlarged cross-sectional view of a main part illustrating the state where the signal lines in the distal end portion of the signal cable according to the first embodiment are connected to terminal portions of the electric circuit board. FIG. 3 is a cross-sectional view illustrating a cross section in the longitudinal direction and a cross section perpendicular to the longitudinal direction of the distal end portion of the signal cable according to the first embodiment. Note that FIG. 3 shows the distal end portion of the signal cable in a preparation stage before being subjected to a processing process described later.

As described above, the signal cable 11 according to the first embodiment is disposed to extend inside the insertion section 6, the operation section 7, and the universal cord 8, and the distal end portion of the signal cable 11 is connected to the electric circuit board 12, on which the image pickup device is mounted, in the distal end portion 6*a* of the insertion section 6.

The configuration of the signal cable 11 will be described below with reference to FIG. 3. Note that, as mentioned above, the signal cable 11 illustrated in FIG. 3 shows the distal end portion in a preparation stage before being subjected to a processing process described later.

Figure 3:
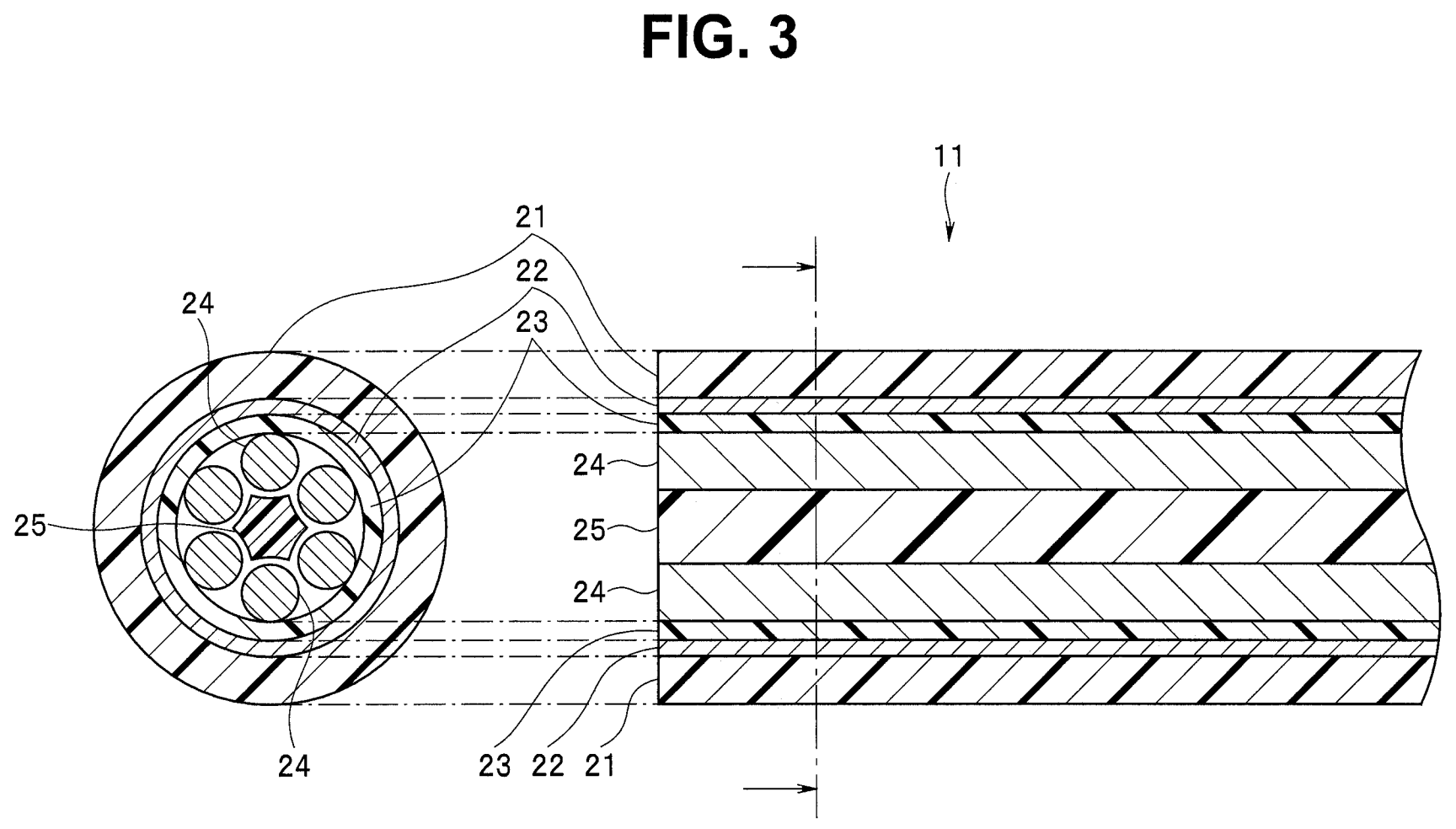

As illustrated in FIG. 3, the signal cable 11 in a state before being subjected to processing according to the present embodiment incorporates a plurality of electric wires 24 each configured of a single wire or a coaxial wire for transmitting predetermined electric signals. The plurality of electric wires 24 are disposed so as to extend in the longitudinal direction from the distal end toward the proximal end side in the substantially central portion in the signal cable 11 with a predetermined interposing line 25 interposed among the electric wires. Note that an insulating material formed of para-aramid fibers made from an aromatic polyamide resin such as Kevlar (registered trademark of DuPont in USA) is employed, for example, as a material for the interposing line 25 in the present embodiment.

The signal cable 11 includes an insulating section 23 that bundles and surrounds the plurality of electric wires 24 or some of the plurality of electric wires 24 and serves as a first insulating layer disposed so as to extend in the longitudinal direction. According to the present embodiment, the insulating section 23 serves as an insulating layer (first insulating layer) made up of so-called binding tape wrapped around the circumference of the bundled electric wires 24. Note that tape made from a material having great insulation properties such as a polyester resin, an epoxy resin, or glass tape is employed as a material for the binding tape in the present embodiment.

The signal cable 11 further includes a shielding section 22 that covers the circumference of the insulating section 23 (binding tape) and serves as a shielding layer that is disposed so as to extend in the longitudinal direction and shields noise and the like. Although some of the plurality of electric wires 24 individually have a shielding function, the shielding section 22 according to the present embodiment has a function of collectively and comprehensively shielding the plurality of electric wires 24. The shielding section 22 is hereinafter also referred to as a comprehensive shield 22.

According to the present embodiment, the signal cable 11 further includes an insulating film 21 that is disposed so as to extend in the longitudinal direction from the distal end toward the proximal end side, covers the circumference of the shielding section 22 (comprehensive shield 22), and serves as a second insulating layer. Note that since the insulating film 21 forms an outermost circumference of the signal cable 11, the insulating film 21 is hereinafter also referred to as a comprehensive outer cover 21.

The distal end portion of the signal cable 11 configured as described above is turned into the state illustrated in FIG. 2 through the processing process described later. As illustrated in FIG. 2, the distal end portions of the plurality of electric wires 24 of the signal cable 11 after being subjected to the processing process are disposed in a state of protruding more toward the distal end side than the distal end portion of the insulating film 21 (comprehensive outer cover 21). The distal end portion of the shielding section 22 (comprehensive shield 22) is disposed nearer to the proximal end side than the distal end portion of the insulating section 23 and the distal end portion of the insulating film 21.

The space between the distal end portion of the insulating section 23 and the distal end portion of the insulating film 21 (comprehensive outer cover 21) is filled with an adhesive 31, as illustrated in FIG. 2. The portion formed by application of the adhesive 31 functions as a fixing portion that fixes the state where the distal end portion of the shielding section 22 (comprehensive shield 22) is disposed in the space between the distal end portion of the insulating section 23 and the distal end portion of the insulating film 21 (comprehensive outer cover 21) so as to maintain the state where the distal end portion of the shielding section 22 is not exposed from the distal end of the insulating film 21.

As illustrated in FIG. 2, the plurality of electric wires 24 of the signal cable 11 have respective distal-end conductive portions 24*a* connected to corresponding terminal portions 13 of the electric circuit board 12 by soldering or the like, in the distal end portion of the insertion section of the endoscope 2 including the signal cable 11 according to the present embodiment.

<Process of Processing Signal Cable 11>

Next, a process of subjecting the distal end portion of the signal cable 11 illustrated in FIG. 3 to predetermined processing to bring the distal end portion into the state illustrated in FIG. 2 will be described with reference to FIGS. 4 to 10.

Figure 4:
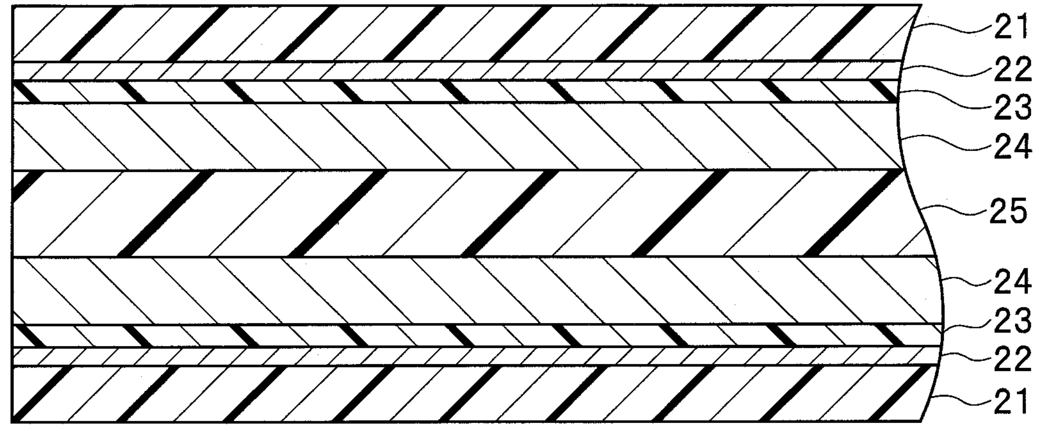
FIG. 4 is a cross-sectional view of the distal end portion of the signal cable according to the first embodiment illustrating the state of preparation stage of a process of processing the distal end portion of the signal cable.

FIG. 4 is a cross-sectional view of the distal end portion of the signal cable according to the first embodiment illustrating the state of preparation stage of the process of processing the distal end portion of the signal cable.

In the preparation stage before processing the distal end portion of the signal cable 11, the signal cable 11 has a form of a general cable in which the respective distal end portions of the comprehensive outer cover 21, the comprehensive shield 22, the insulating section 23, and the plurality of electric wires 24 are aligned with each other, as illustrated in FIG. 4.

Figure 5:
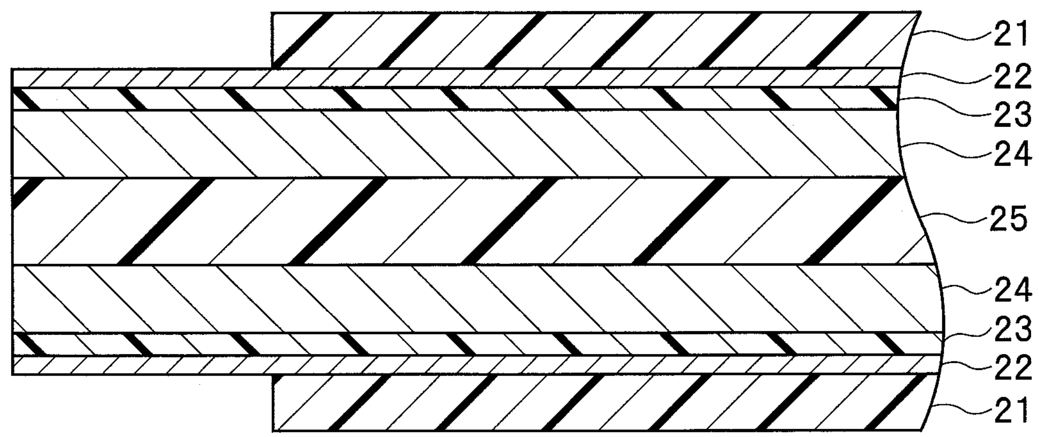
FIG. 5 is a cross-sectional view of the distal end portion of the signal cable according to the first embodiment illustrating the state of the distal end portion in a step of cutting a comprehensive outer cover in the process of processing the distal end portion of the signal cable.
Figure 6:
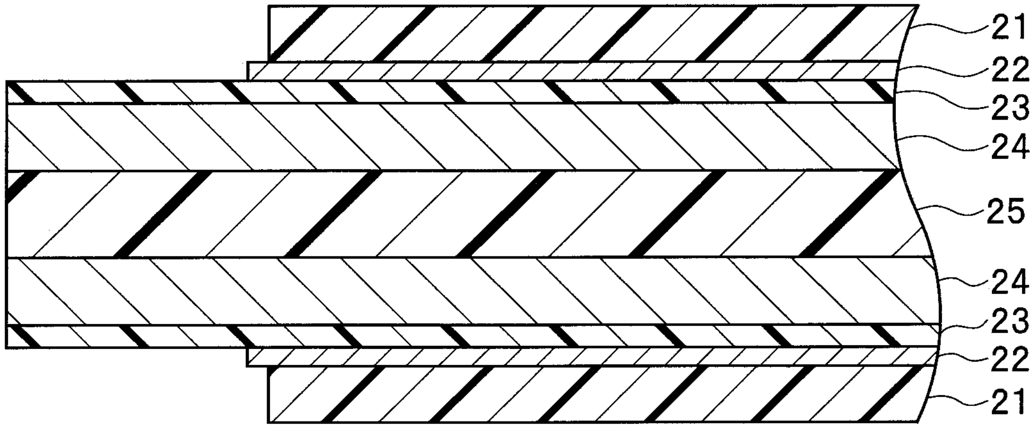
FIG. 6 is a cross-sectional view of the distal end portion of the signal cable according to the first embodiment illustrating the state of the distal end portion in a step of cutting a comprehensive shield in the process of processing the distal end portion of the signal cable.

From the distal end portion of the signal cable 11 in the preparation stage, the comprehensive outer cover 21 is cut first as illustrated in FIG. 5, and next the comprehensive shield 22 is cut as illustrated in FIG. 6. In this process, the distal end of the comprehensive shield 22 is cut away such that a distal end of the comprehensive shield 22 is positioned approximately the same as a distal end of the comprehensive outer cover 21 having been cut.

Figure 7:
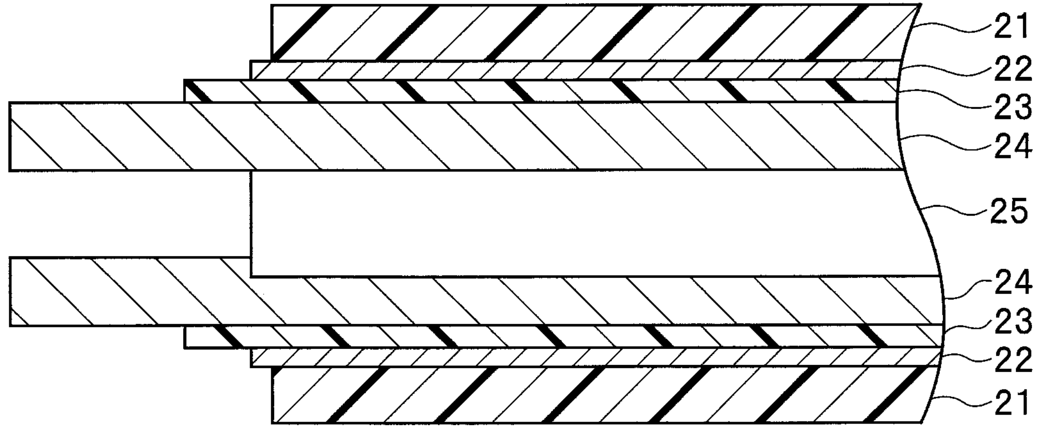
FIG. 7 is a cross-sectional view of the distal end portion of the signal cable according to the first embodiment illustrating the state of the distal end portion in a step of cutting a binding tape serving as an insulating layer provided on the circumference of a plurality of electric wires bundled together in the process of processing the distal end portion of the signal cable.

Subsequently, the insulating section 23 (binding tape) serving as the insulating layer provided on the circumference of the bundled electric wires 24 and the interposing line 25 are cut, as illustrated in FIG. 7. In the process, a distal end portion of the insulating section 23 (binding tape) is reliably reserved.

Figure 8:
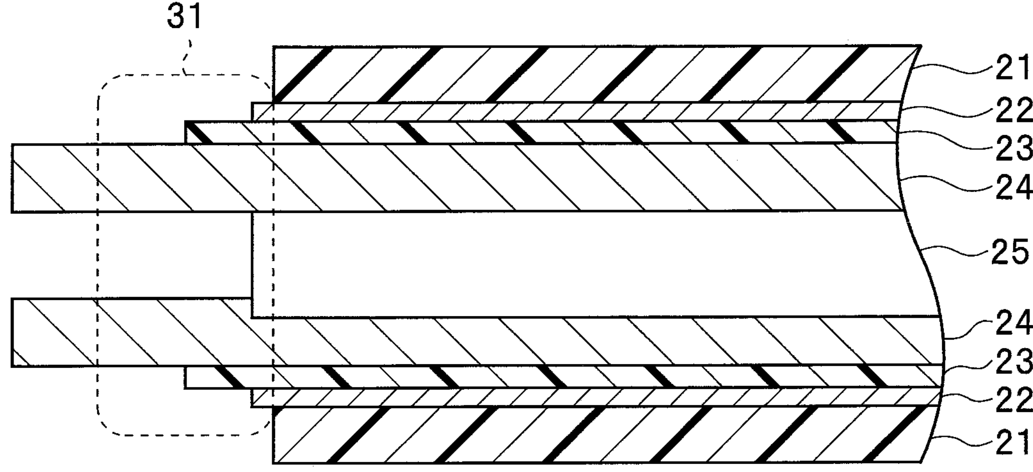
FIG. 8 is a cross-sectional view of the distal end portion of the signal cable according to the first embodiment illustrating the state of the distal end portion in a step of applying an adhesive for fixing the comprehensive shield and the binding tape, which have been cut, in the process of processing the distal end portion of the signal cable.

Next, the adhesive 31 is applied to cover the distal ends of the comprehensive shield 22 and the binding tape 23, which have been cut, at the distal end portion of the signal cable 11, as illustrated in FIG. 8. The portion formed by application of the adhesive 31 serves as the fixing portion that fixes the distal ends of the comprehensive shield 22 and the binding tape 23.

Figure 9:
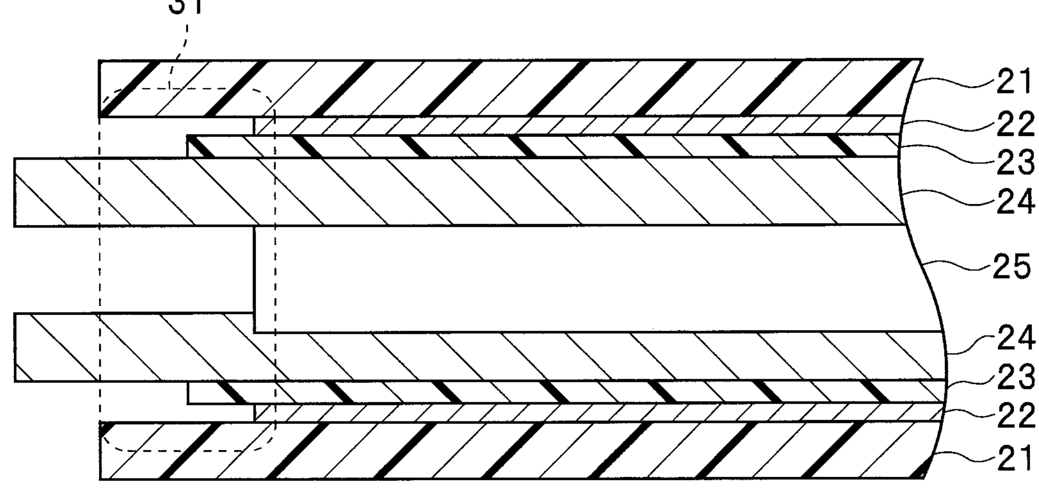
FIG. 9 is a cross-sectional view of the distal end portion of the signal cable according to the first embodiment illustrating the state of the distal end portion in a step of drawing forward the comprehensive outer cover after application of the adhesive in the process of processing the distal end portion of the signal cable.
Figure 10:
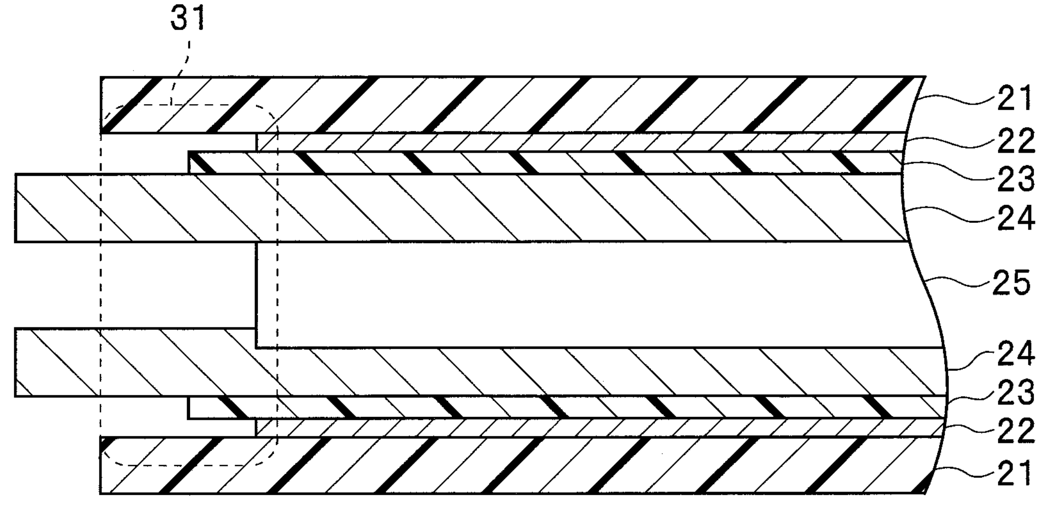
FIG. 10 is a cross-sectional view of the distal end portion of the signal cable according to the first embodiment illustrating the state where the adhesive has cured and the internal components are fixed in the process of processing the distal end portion of the signal cable.

After application of the adhesive 31 to the distal end portion of the signal cable 11, the comprehensive outer cover 21 is drawn forward as illustrated in FIG. 9. In this process, the adhesive 31 squeezed out of the distal end of the signal cable 11 is wiped off.

After the adhesive 31 has cured and the internal components such as the comprehensive shield 22 and the insulating section 23 (binding tape 23) are fixed (FIG. 10), the distal end portions of the comprehensive shield 22 and the binding tape 23 are covered by the adhesive 31 and are prevented from exposure to the outside.

After the processing process described above, only the distal end portions of the plurality of electric wires 24 are exposed from the distal end portion of the signal cable 11, as illustrated in FIG. 2. Next, the distal end portions 24*a* of the plurality of electric wires 24 are connected to corresponding terminal portions 13 of the electric circuit board 12.

Figure 13:
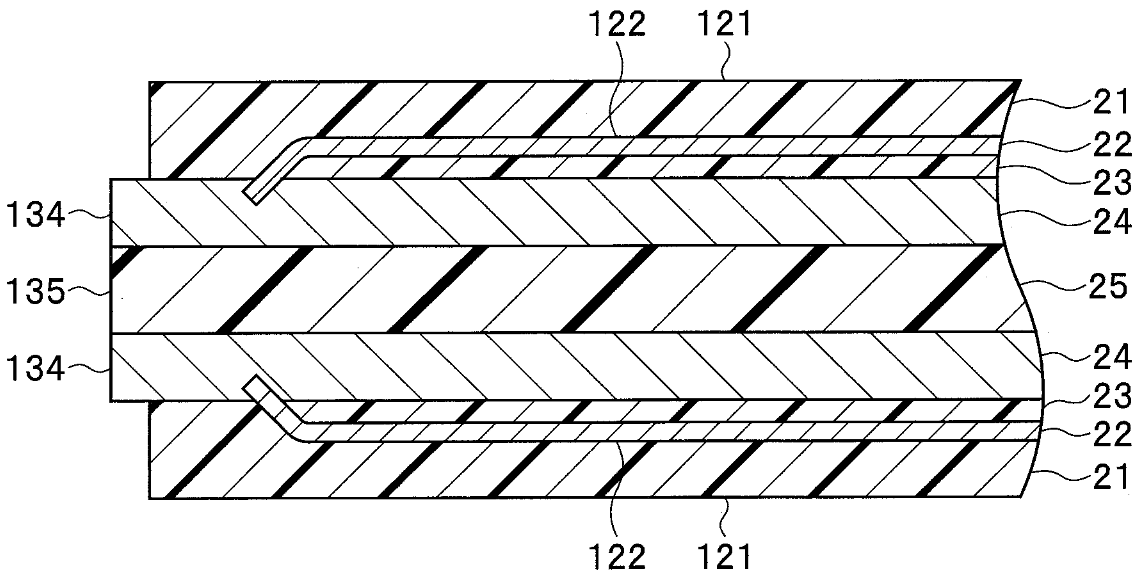
FIG. 13 is a cross-sectional view of a distal end portion of a signal cable disposed in a distal end portion of an insertion section of an endoscope illustrating the state where a shielding section is not positionally restricted inside a comprehensive outer cover of the signal cable.

It is now assumed that the process of drawing the comprehensive outer cover 21 is performed without any consideration given about the position of the comprehensive shield 22 and without the process of fixing the comprehensive shield 22 and the binding tape 23 with use of the adhesive 31 or the like, in this case, for example, the end portion of a shield 122 inside an outer cover 121 is not restricted as illustrated in FIG. 13 and hence the distal end of the shield 122 may come into contact with an internal signal line 134 (reference numeral 135 indicates an interposed line), potentially leading to a defect caused by, for example, a short-circuit between the shield 122 and the signal line 134 during a procedure of connecting the plurality of electric wires 24 of the signal cable 11 to the electric circuit board 12.

In contrast, the signal cable 11 according to the first embodiment produced through the processing process described above allows the positions of the comprehensive shield 22 and the insulating section 23 (binding tape) inside the comprehensive outer cover 21 to be reliably restricted, and therefore, the end portion of the comprehensive shield 22 can be prevented from coming loose, work efficiency of connection between the plurality of electric wires 24 and the electric circuit board 12 can be improved, and a defect caused by, for example, a short-circuit between the comprehensive shield 22 and the plurality of electric wires 24 can be prevented.

Figure 14:
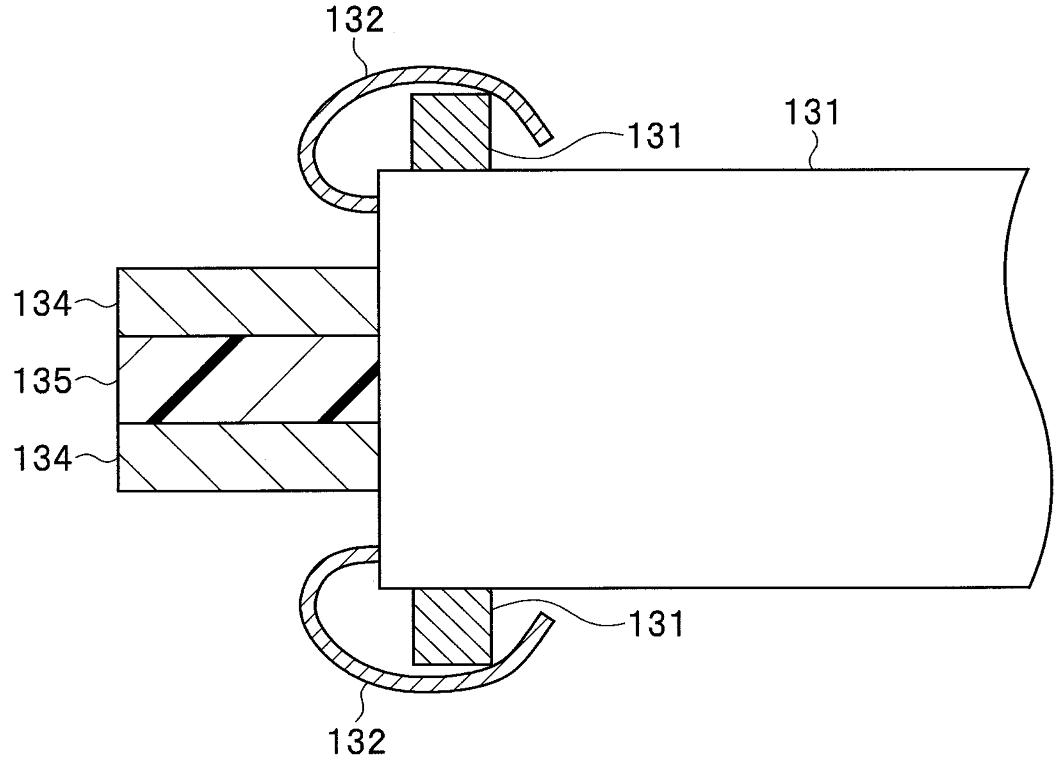
FIG. 14 is a cross-sectional view of a distal end portion of a signal cable disposed in a distal end portion of an insertion section of an endoscope illustrating the state where a ring member is disposed for fixing a shielding section on the circumference of a comprehensive outer cover of the signal cable.

For eliminating the defect mentioned above with reference to FIG. 13, there is another conceivable way of restricting the position of the shield line 132 with, for example, a ring-shaped conductive member 131 fitted onto the outer cover 121 of the signal cable, temporarily drawing forward a shield line 132 disposed inside the outer cover 121 and then bending hack the shield line 132 along the ring-shaped conductive member 131, as illustrated in FIG. 14. In this case, although this configuration can prevent a defect caused by, for example, a short-circuit between the shield line 132 and an internal signal line 134 (reference numeral 135 indicates an interposed line), the ring-shaped conductive member 131 additionally provided to the outer cover 121 of the signal cable causes a problem of increase in the number of components and increase in outer diameter of the signal cable.

As described above, the signal cable 11 according to the first embodiment and the endoscope 2 including the signal cable 11 exhibit such an effect that work efficiency of connection of the signal cable 11 can be improved and that deterioration in quality can be prevented, without dimensional increase in the radial direction of the signal cable 11.

Second Embodiment

Figure 12:
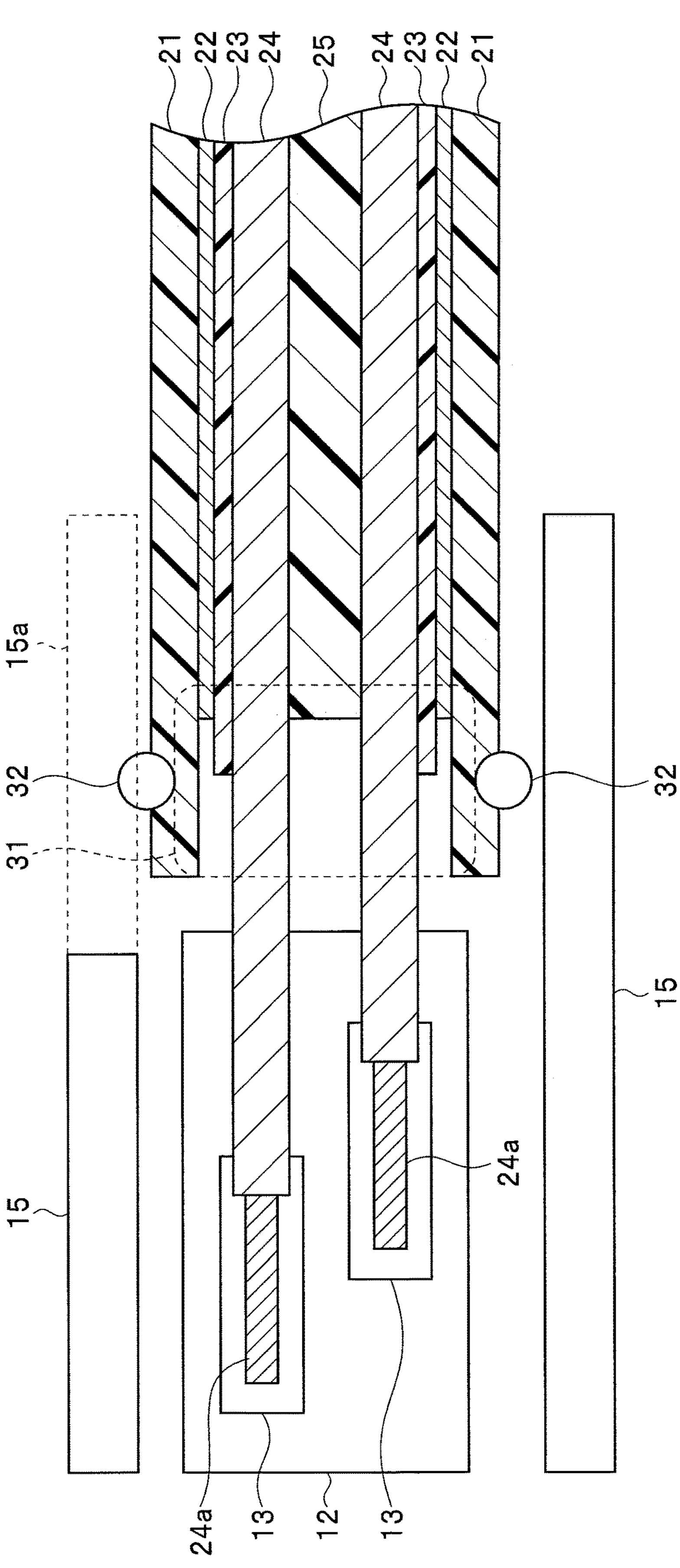
FIG. 12 is an explanatory diagram illustrating the state where signal lines of the distal end portion of the signal cable according to the second embodiment are connected to terminal portions of an electric circuit.

Next, a second embodiment of the present invention will be described,

FIG. 12 is an explanatory diagram illustrating the state where signal lines in a distal end portion of a signal cable according to the second embodiment of the present invention are connected to terminal portions of an electric circuit.

Figure 11:
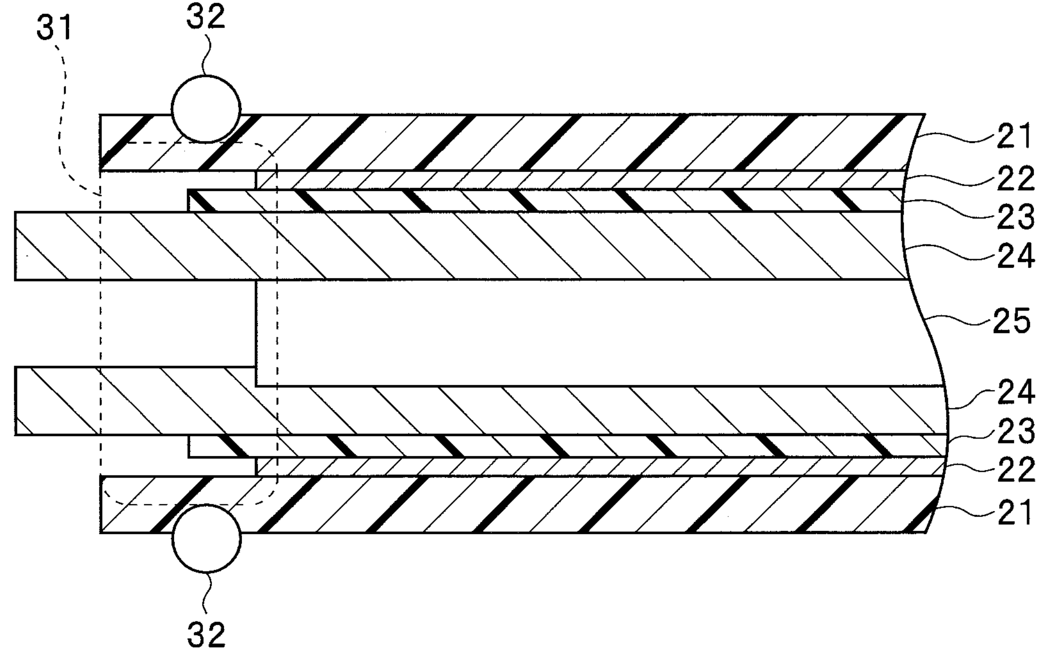
FIG. 11 is a cross-sectional view of a distal end portion of a signal cable according to a second embodiment of the present invention illustrating the state of the distal end portion in a step of externally binding a comprehensive outer cover with a thread after an adhesive has cured in a process of processing the distal end portion of the signal cable.

FIG. 11 is a cross-sectional view of the distal end portion of the signal cable according to the second embodiment illustrating the state of the distal end portion in a step of externally binding a comprehensive outer cover with a thread after an adhesive has cured in a process of processing the distal end portion of the signal cable.

Since the basic configurations of the signal cable according to the second embodiment and an endoscope including the signal cable are the same as the configurations according to the first embodiment, only the difference is described bel ow.

A signal cable 11 according to the second embodiment is processed in the same way as the signal cable 11 according to the first embodiment throughout the processing process illustrated in FIG. 4 to FIG. 10. The signal cable 11 according to the second embodiment is further subjected to a step of externally binding the comprehensive outer cover 21 with a thread 32 to additionally bind the portion fixed with an adhesive 31 from the outside as illustrated in FIG. 11, in addition to the processing process illustrated in FIG. 4 to FIG. 10.

The signal cable 11 according to the second embodiment has internal components such as a comprehensive shield 22 and a binding tape 23 which are more reliably fixed through an additional tightening step with the thread 32.

Although the second embodiment achieves such an effect that the distal end portions of the comprehensive shield 22 and an insulating section 23 (binding tape) are more reliably fixed since the comprehensive outer cover 21 is externally tightened by the thread 32 at the portion corresponding to the adhesive 31 as described above, the outer diameter is slightly increased because the thread 32 is positioned outside the comprehensive outer cover 21.

In view of the above problem, the second embodiment is configured to prevent the increase in outer diameter by employing a cover 15 that covers the comprehensive outer cover 21 of the signal cable 11 and an electric circuit board 12 to which the signal cable 11 is connected, in which the cover 15 is cut out at a portion 15*a* where the cover would face the thread 32 (that is, would interfere with the thread 32), as illustrated in FIG. 12.

The signal cable 11 according to the second embodiment and the endoscope 2 including the signal cable 11 configured as described above achieve such an effect that the distal end portions of the comprehensive shield 22 and the insulating section 23 (binding tape) are more reliably fixed without increase in outer diameter of an insertion section of the endoscope including the signal cable 11.

The present invention is not limited to the above-described embodiments, and can be modified or altered in various ways without changing the gist of the present invention.

What is claimed is:

1. A signal cable comprising:

a plurality of electric wires each having a distal end and a proximal end, each of the plurality of electric wires are configured to extend in a longitudinal direction from a respective distal end to a respective proximal end and each of the plurality of electric wires are configured to transmit electricity;

a first insulating layer that surrounds the plurality of electric wires and is disposed so as to extend in the longitudinal direction;

a shielding layer that covers a circumference of the first insulating layer and is disposed so as to extend in the longitudinal direction;

a second insulating layer that covers a circumference of the shielding layer and is disposed so as to extend in the longitudinal direction; and a fixing portion that fixes a distal end of the shielding layer, wherein the distal ends of each of the plurality of electric wires are disposed so as to protrude further in the longitudinal direction than a distal end of the second insulating layer, the distal end of the shielding layer is disposed nearer to a proximal end of the first insulating layer than to a distal end of the first insulating layer, the distal end of the shielding layer is disposed nearer to a proximal end of the second insulating layer than to the distal end of the second insulating layer, and the fixing portion fixes the distal end of the shielding layer in a space between the distal end of the first insulating layer and the distal end of the second insulating layer so as to maintain a state where at least the distal end of the shielding layer is not exposed from the distal end of the second insulating layer.

2. The signal cable according to claim 1, wherein the fixing portion is formed to include an adhesive that fills the space.

3. The signal cable according to claim 2, wherein the fixing portion is formed by a thread wound around a circumferential portion of the second insulating layer while a force of tightening the second insulating layer is applied, and the thread fixes the adhesive between a distal end portion of the first insulating layer and the distal end portion of a second insulating layer by application of the force.

4. The signal cable according to claim 3, further comprising a cover that covers at least the distal end portion of an outer-surface of the second insulating layer, wherein the cover has an inner surface side provided with a cutout that engages with the thread disposed on a circumference of the second insulating layer.

5. An endoscope comprising:

an electric circuit board;

a plurality of electric wires each having a distal end and a proximal end, each of the plurality of electric wires are configured to extend in a longitudinal direction from a respective distal end to a respective proximal end and each of the plurality of electric wires are configured to transmit electricity to the electric circuit board;

a first insulating layer that surrounds the plurality of electric wires and is disposed so as to extend in the longitudinal direction;

a shielding layer that covers a circumference of the first insulating layer and is disposed so as to extend in the longitudinal direction;

a second insulating layer that covers a circumference of the shielding layer and is disposed so as to extend in the longitudinal direction; and a fixing portion that fixes a distal end portion of the shielding layer, wherein the distal ends of each of the plurality of electric wires are disposed so as to protrude further in the longitudinal direction than a distal end of the second insulating layer, the distal end of the shielding layer is disposed nearer to a proximal end of the first insulating layer than to a distal end of the first insulating layer, the distal end of the shielding layer is disposed nearer to a proximal end of the second insulating layer than to the distal end of the second insulating layer, and the fixing portion fixes the distal end of the shielding layer in a space between the distal end of the first insulating layer and the distal end of the second insulating layer so as to maintain a state where at least the distal end of the shielding layer is not exposed from the distal end of the second insulating layer.

* * * * *